United States Patent [19]

Key

[11] Patent Number: 4,576,171

[45] Date of Patent: Mar. 18, 1986

[54] ANIMAL IMMOBILIZING APPARATUS AND METHOD

[76] Inventor: Richard Key, 1807 Iowa St., Costa Mesa, Calif. 92626

[21] Appl. No.: 578,269

[22] Filed: Feb. 8, 1984

[51] Int. Cl.$^4$ .............................................. A61N 1/32
[52] U.S. Cl. ..................................... 128/421; 128/1 C
[58] Field of Search .................. 128/419 R, 421, 422, 128/423, 1 C, 908

[56] References Cited

U.S. PATENT DOCUMENTS

| | | | |
|---|---|---|---|
| 3,516,413 | 6/1970 | McDonald et al. | 128/422 |
| 3,718,132 | 2/1973 | Holt et al. | 128/1 C |
| 4,088,141 | 5/1978 | Niemi | 128/421 |
| 4,237,896 | 12/1980 | Lines | 128/421 |

FOREIGN PATENT DOCUMENTS 1220031  1/1960  France ................................. 128/1 C Primary Examiner—William E. Kamm
Attorney, Agent, or Firm—George F. Bethel; Patience K. Bethel

[57] ABSTRACT

An electronarcotic current is delivered to an animal through improved probes in order to immobilize the animal. The electronarcotic current is adjusted based on the intrinsic resistance of the animal which is used to provide a feedback current for adjustment of the electric current. The electronarcotic current is also modulated with a duty cycle at a slave frequency which in turn is further modulated to form a group repetition rate as determined by a master frequency. Energy introduced into the animal may be minimized after initial mobilization to thereby hold the electronarcotic effect with minimal adverse effect of pulmonary and cardiovascular functioning.

10 Claims, 11 Drawing Figures

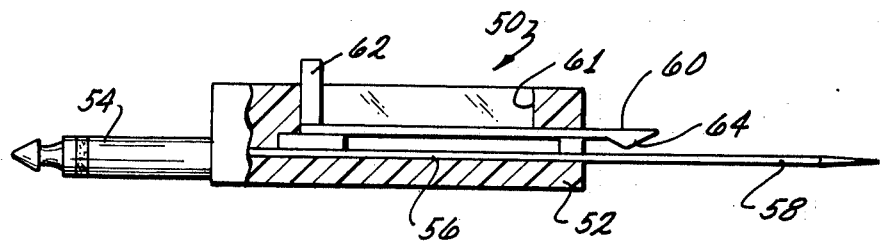
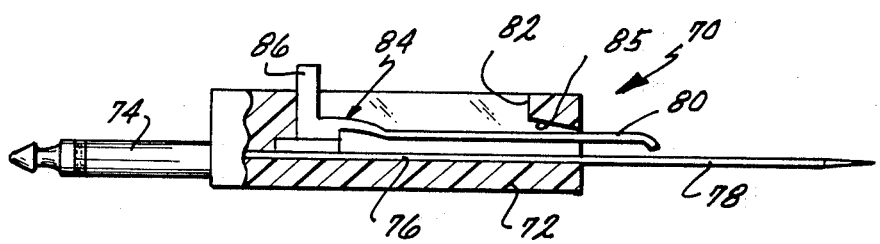
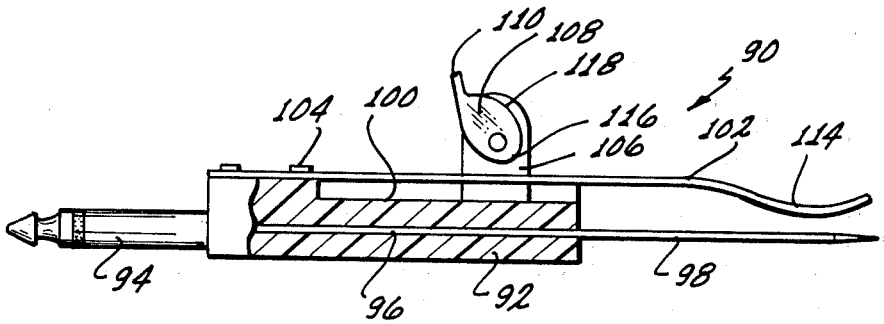
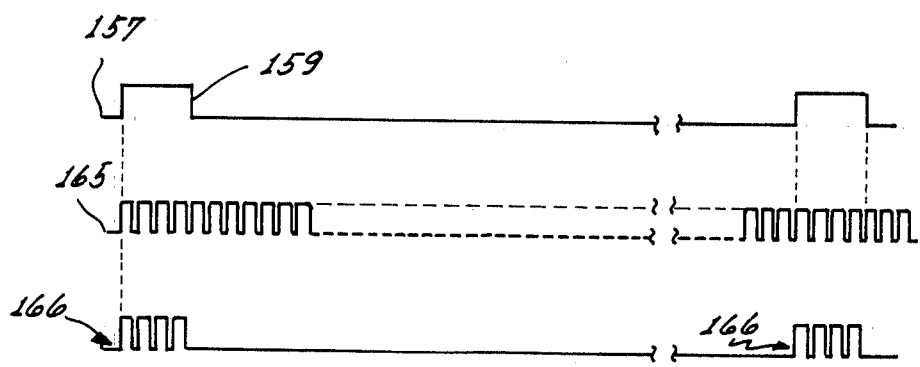

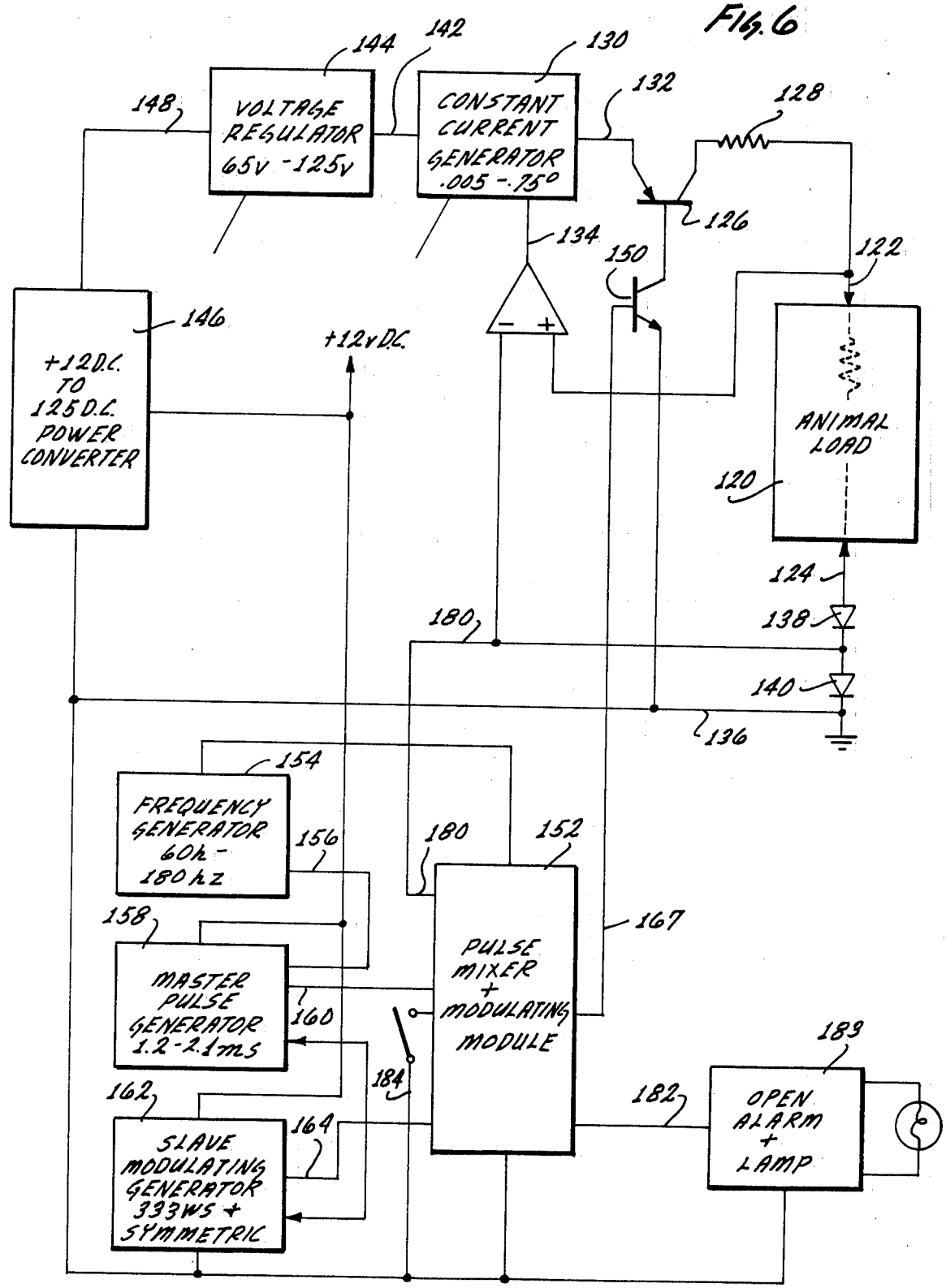

ANIMAL IMMOBILIZING APPARATUS AND METHOD

BACKGROUND OF THE INVENTION

1. Field of the Invention

This invention relates to a means for and method of handling animals and in particular to the immobilization and anesthetization for the purposes of husbandry or veterinary medicine.

There has been a longfelt need for immobilizing animals for veterinary purposes to allow for routine treatments, such as shearing or to provide special diagnostic or veterinary treatment. Traditionally, chemical anesthetics have been used, particularly with wild animals, to immobilize the animal for a sufficient time to allow access for treatment. However, it is well known that numerous risks and complications can occur in the case of chemical anesthesia, and injection of the initial immobolizing dose is often difficult to control. As a result, in many cases, chemically anesthetized animals are sometimes overdosed to the temporary or permanent damage or loss of the animal. In any case, the recovery of a chemically anesthetized animal requires a period of time and it is thought that repeated anesthetic doses may have a cumulative adverse effect.

As an alternative to chemical anesthetics, the prior art has devised various means and apparatus for providing electroanethesia which is a technique of passing electric current through selected portions of the animal's body to result in total relaxation or interference and blockage of the animals neural muscular system. See for example Lines, "Immobilizing Animals", U.S. Pat. No. 4,237,895.

However, such prior art means and methods for producing electronarcosis generally apply a single voltage level to the animal during the electronarcotic period. After initial immobilization, the animal often can stiffen to such an extent that breathing is temporarily arrested. In some cases, the voltage and current settings required for initial immobilization will ultimately suppress respiration either causing the animal to succumb by suffocation or possibly cardiac malfunction.

Furthermore, it has been found that different sizes of animals require different currents in order to initiate electronarcosis and immobilization and that the immobilizing parameters may vary among different animals of similar sizes or among individuals of the same species of animal. No analytical model is yet available which can predict the exact electronarcotic voltage and current required for any given species or individual within a species.

In addition, electrical contact made between the animal and the electronarcotic source sometimes varies between animals or between repeated contacts with the same animal. The electrical connection made to the animals body must therefore be secure and repeatable if the electronarcotic, current and voltage for any given animal are to be repeatable as well.

Therefore, what is needed is an apparatus and method for producing electronarcosis in an animal in a manner which avoids traumatizing the animals respiratory or cardiac functions; which provides continuous amounts of sufficient electronarcotic voltage and current; which automatically accommodates to the different electronarcotic thresholds observed between different species of animals and individuals within a single species; and which can be reproducibly peformed with any given animal.

BRIEF SUMMARY OF THE INVENTION

The present invention is an apparatus for making and maintaining electrical contact to an animal comprising a body, a substantially rigid electrode extending from the body for subcutaneous insertion within the animal and a barbed extension connected to the rigid electrode. The rigid electrode is arranged and configured for electrical coupling to an electronarcotic signal. The barbed extension forms a forward bending hook with a sharp point wherein the rigid electrode is subcutaneously implanted within the animal. The forward bending portion of the barbed electrode is nonevasively disposed against a fold of skin of the animal with the sharp point of the barbed electrode engaging the fold of skin to thereby positively maintain the apparatus and the rigid electrode in contact with the animal.

In another embodiment the apparatus for making and maintaining electrical contact with the animal for the purpose of effecting electronarcosis comprises a body, a substantially rigid electrode extending from the body and a resilient clip. The rigid electrode again is adapted for subcutaneous insertion within the animal and is further arranged and configured for coupling to an electronarcotic signal. The resilient clip is cantilevered forwardly over the rigid electrode and has at least one configuration wherein the clip is parallel to the rigid electrode over at least a substantial length or portion of the rigid electrode.

The invention also comprises an apparatus for applying an electronarcotic signal to the animal comprising an electrode for making and maintaining electrical contact with the animal as described above and a source for generating the electronarcotic signal. The source is coupled to the electrode and is particularly characterized by including a feedback loop for adjusting the electronarcotic signal. By virtue of this combination of circular elements, the intrinsic electrical resistance path through the animal is included as part of the feedback loop of the source. Therefore, individual variations among animals is automatically compensated by adjustment of the source which generates the electronarcotic signal by including the intrinsic resistance of the animal in the feedback loop at the source. More particularly, the source generates a voltage in the range of approximately 60–125 volts DC with a current approximately in the range of 5–750 milliamps. Electronarcotic signals generated by the source are modulated at master pulse rate in the range of approximately 60–180 hertz. A pulse width of approximately 1.2–2.1 milliseconds characterizes the master pulse. The source further modulates the electronarcotic master pulse signal at a higher slave frequency pulse rate and with a preselected duty cycle. In particular, the source generates the electronarcotic signal with a modulation having pulses reproduced at a group rate of approximately the same order of magnitude as the neuromuscular signals within the animal itself. The pulses are provided with a selected duty cycle in order to reduce the total energy provided by the source through the electrode into the animal.

The present invention also includes a method for immobilizing an animal by passing an electronarcotic current through the animal. The method comprises steps of generating a direct current at a preselected voltage for application to the animal. Next, the direct current is applied to the animal. A portion of the current applied to the animal is fed back to the source generating the direct current. The direct current generated by the source is then adjusted and applied to the animal in response to the current fed back from the animal. By reason of this combination of steps the intrinsic resistance of the animal is included in a feedback path of the source for generating the direct current. The amplitude of the direct current delivered to the animal is thus adjusted to accommodate the individual electrical characteristics of the animal.

BRIEF DESCRIPTION OF THE DRAWINGS

FIG. 2b is a plan view taken through lines 2b—2b of FIG. 2a.

FIG. 2c is an end sectional view in enlarged scale taken through lines 2c—2c of FIG. 2a.

FIG. 3 is a side sectional view of a third embodiment of a probe incorporating the invention.

FIG. 4 is a side sectional view of a fourth embodiment of a probe incorporating the invention.

FIG. 5 is a side sectional view of a probe showing a fifth embodiment incorporating the invention.

FIG. 6 is a block diagram of a circuit incorporating the invention for use in connection with any one of the probes shown in FIGS. 1a–c–5.

FIG. 7 is a timing diagram of an electronarcotic current and voltage produced by the circuitry of FIG. 6.

The invention and its various embodiments may be better understood together with its mode of operation by considering the following description in light of the above Figures.

DETAILED DESCRIPTION OF THE PREFERRED EMBODIMENTS

According to the invention, the amount of energy needed to quickly immobilize an animal is far in excess of that level needed to sustain immobilization or electronarcosis. At least four such recognizable electronarcotic energy levels can be defined.

The first energy level is a blocking energy level which is the energy level needed to inhibit nervous communication to the muscles and to block the sensation of pain. Generally, the application of a blocking energy level is best applied quickly and decisively in order to avoid any opportunity for panic in the animal.

The second energy level is a holding energy level which is the minimum energy needed to maintain anesthesia for a period of time for the desired husbandry procedure. The holding energy level can be much lower than the blocking energy level and can be the level which will allow the animal to react to auditory stimulus, to freely respire and to continue with involuntary bodily functions. By reduction of the blocking energy level to the holding energy level according to the invention, the practitioner can practice husbandry procedures for a much greater period of time than before achievable.

The third energy level is a post-procedural energy level which is the energy level required during which time the animal will be prepared to return to the herd or other post-procedural activity. The post-procedural energy level is maintained at the holding level or in the case of very large animals in may be necessary to return temporarily to the blocking energy level for the safety of a practitioner.

Finally, the fourth level is the post-electroanalgesic level. The post-analgesic level is generally the post-electronarcosis state of the animal and may persist for some time after the procedures have been completed. A post-analgesic level may last up to several hours in length while the energy level is gradually diminished to zero or substantially zero.

In order to apply and practice the four electronarcotic levels briefly described above according to the methodology of the invention, it is necessary that a constant electrical contact be made with the animals neural system without the possibility of variable or intermittent contact. Poor or intermittent contact with the body fluids and muscular tissue of the animal will result in a substantial part of the energy which is transferred to the animal being dissipated at the point of highest resistance, usually the point of contact, and will therefore result in pain and panic to the animal.

Figure 1:
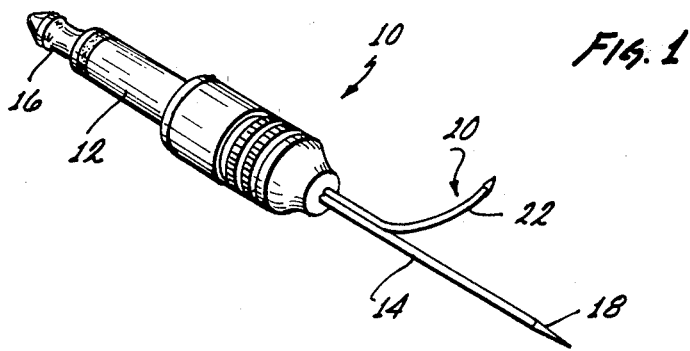
FIG. 1 is a side elevational view of a first embodiment of a probe incorporating the invention.

Turn first to the probe of FIG. 1 which provides means for making secure electrical contact with the animal's tissue. The embodiment of FIG. 1 is shown as a probe for use with very large animals, although it could be adapted according to the spirit and scope of the present invention to be used with smaller animals as well. Probe 10 is comprised of a metallic body 12 which insulatively incorporates a central electrode and a conventional male electrical contact 16. Electrical connector 16 is electrically coupled to electrode 14 which at its opposing end is electrically coupled to straight spear point 18. Generally, body 12 is insulatively separated from electrode 14 and spear point 18 so that electrical energy as described in connection with FIGS. 6 and 7 below, coupled to electrode 14 and point 18 through connector 16, is not coupled to body 12. Body 12 provides a convenient handle and transition between power cords (not shown) which connect with connector 16 and are coupled to spear point 18, which is subcutaneously implanted within the animal to effect secure electrical contact with its internal tissues.

In the illustrated embodiment, spear point 18 is approximately three inches long and is further provided with a hooked barb 20. Barb 20 is welded or otherwise electrically and mechanically coupled to the base of straight electrode 14 and is shaped into a backward curving barb terminating in a sharp point. Therefore, as spear point 18 is subcutaneously inserted into the fatty tissue of the animal, the forward rounded portion 22 of barb 20 will be pressed against the outside skin of the fatty tissue, eventually pushing a substantial part of the barb 20, including its sharp tip, into a fold of the fatty skin. As the practitioner then releases probe 10, the resiliency of the fatty tissue will tend to force probe 10 out. However, barb 20 pricks or hooks the fold of fatty skin as it moves outwardly thereby retaining probe 10 and, in particular, spear point 18 in the tissue in its substantially and fully inserted configuration. However, when it is desired to remove probe 10, it is easily released from the tissue by slightly forcing probe 10 inward until rounded portion 22 of barb 20 again depresses a fold of the skin which causes the tip of barb 20 to release from the skin thereby permitting the convenient manual withdrawal of probe 10. The attachment of probe 10 to the animal is surprisingly secure. The probe is rugged and simple in construction and yet provides the nonintermittent electrical contact with the bodily tissue of the animal which is necessary for the effective practice of electronarcosis.

Figure 2A:
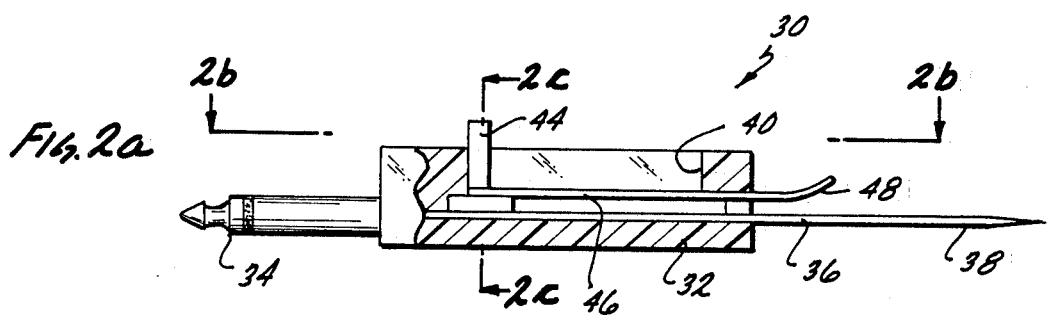
FIG. 2a is a side sectional view of a second embodiment of a probe incorporating the invention.
Figure 2B:
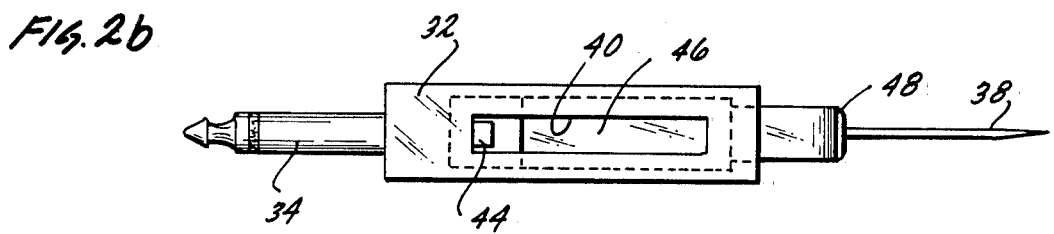
Figure 2C:
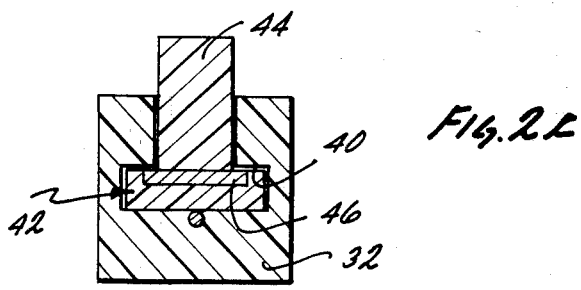

Turn now to a second embodiment of a probe as shown in FIGS. 2a-2c. The probe, generally denoted by reference numeral 30, includes a body 32 again which includes a conventional electrical male terminal 34. Terminal 34 is connected to a central electrode 36 extending through body 32 and insulatively separated therefrom. Central electrode 36 again terminates in a straight spear electrode 38 which is subcutanesously implanted within the animal in fatty tissue. Body 32 has a T-slot 40 longitudinally defined along its length as best illustrated in FIG. 2c which is an enlarged cross section taken through lines 2c-2c of FIG. 2a. Disposed within T-shaped slot 40 within body 32 is a similarly T-shaped slide 42. Slide 42 is arranged and configured to be smoothly and frictionally slid within mating slot 40 by application of a longitudinal manual force to handle 44. Handle 44, as illustrated in FIG. 2c in cross section is connected to a flat resilient member 46 which longitudinally extends through the length of slot 40 as best seen in plan view in FIG. 2b. Resilient member 46 extends from body 32 to form an uplifted shoe termination 48 extending from the same end of body 32 as electrode 38.

Thus, a longitudinal manual force applied to handle 44 slides handle 44 and resilient member 46 forwardly within slot 40 thereby extending member 46 forwardly over and parallel to extended electrode 38. It is therefore intended that probe 30 be grasped and electrode 38 subcutaneously disposed under the skin of the animal. Thereafter, manual force is applied to handle 44 moving resilient member 46 outwardly across the skin of the animal above electrode 38 which is buried therebeneath. Shoe 48 provides for a smooth sliding contact of member 46 across the animals skin as member 46 is used to close or squeeze on the layer of skin disposed between electrode 38 and the extended clip formed by resilient member 46.

A third embodiment of the invention is illustrated in side sectional view in FIG. 3 which is a further modification of a probe of the type as shown in connecton with FIGS. 2a-2c. In FIG. 3 the probe, generally denoted by reference numeral 50 again includes a body 52 which is insulatively separated from and which incorporates an electrical connector 54 coupled to a central electrode 56. Central electrode 56 in turn is coupled to a substantially rigid extending electrode 58 which longitudinally extends from body 52 beneath a slidable resilient clip member 60 similar to resilient member 46 of the second embodiment of FIGS. 2a-2c. As in the case of the second embodiment, clip member 60 is disposed within a mating groove 61 within body 52 and is manually operated through its connection to a slidable handle 62. The third embodiment of FIG. 3 differs from that of FIGS. 2a-2c in that clip member 60 is provided with a bulbous termination 64 which provides smooth non-abrasive contact with the animal's skin. In addition, bulbous member 64 narrows the clearance between resilient clip member 60 and substantially rigid electrode 58 so that, even with modest subcutaneous disposition of electrode 58 under the skin of the animal, bulbous termination 64 will cause clip member 60 to be flexed backwardly thereby creating a tightening or clipping attachment of probe 50 to the animal as clip member 60 is extended by a longitudinal force manually applied to handle 62 after electrode 58 has been subcutaneously embedded.

A fourth embodiment of the probe is shown in side sectional view in FIG. 4 wherein the probe, generally denoted by reference numeral 70, again includes a body 72, an electrical end connector 74 coupled to a central electrode 76, and a substantially rigid exposed electrode 78 extending from body 72 and connected to central electrode 76. In the case of the fourth embodiment shown in FIG. 4 a clip member 80 is disposed within a longitudinal slot 82 defined within the body 80 and includes a sliding cam portion denoted by reference numeral 84. Clip member 80 again is connected or integrally formed with a handle 86. Handle 86 is immediately adjacent to cam portion 84 which provides a curved surface which resiliently bears against the upper surface 85 of slot 82 within body 72. Slot 82 is formed within body 72 with a sloping surface having an initial vertical height which is the same as or slightly greater than the vertical height of cam portion 84. Slot 82 narrows at its opposing end to a height substantially equal to the height of a straight portion of clip member 80. Thus, as a manual longitudinal force is applied to handle 86, clip member 80 is longitudinally displaced forwardly and above fixed electrode 78 in the same manner as described in the previous embodiments, except that cam portion 84 will wedge within sloping slot 82 against surface 85 to temporarily fix clip member 80 within body 72. As before, clip member 80 in combination with electrode 78 will provide a means of attaching electrode 78 to the animal. The embodiment of FIG. 4 offers the advantage over the embodiments of FIGS. 2a-2c and 3 in that a separate means is provided for securing the clip member 60 relative to body 72 of the probe 70 as well as including a means for fixing electrode 78 to the point of insertion on the animal.

A fifth embodiment of a probe, generally denoted by reference numeral 90, is shown in side sectional view in FIG. 5. Once again, probe 90 includes a body 92 in which a conventional electric connector 94 is incorporated and connected to an insulated central electrode 96. Central electrode 96 runs the longitudinal length of body 92 and terminates in a substantially rigid exterior electrode 98. However, as shown in FIG. 5, a recessed portion 100 of probe 90 is defined at that end of probe 90 nearest electrode 98 and provides a means by which clip member 102 is cantilevered over body 92 and electrode 98. In the fifth embodiment of FIG. 5, clip member 102 is affixed by conventional means, such as a screw or rivet 104 to body 92 and cantilevered across portion 100. Clip member 102 is thus fixed in place and extended across body 92 and forwardly above electrode 98. However, the separation between electrode 98 and clip member 102 is substantially greater in the embodiment of FIG. 5 than in the previously described embodiments. Body 92 also includes a cam post 106 connected or formed therewith to which is rotatably pivotted an eccentric cam 108 rotated by a rigid lever 110.

Electrode 98 is subcanteously implanted in the fatty tissue of the subject animal while resilient clip member 102 slides above the skin fold in a nonabrasive manner with the assistance of curved terminating shoe portion 114. After probe 90 is placed in the desired position, lever 110 is rotated in a clockwise fashion as shown in FIG. 5 thereby rotating eccentric cam 108 against the upper surface of resilient clip member 102. This forces clip member 12 downwardly, squeezing the skin fold between electrode 98 and clip member 102. Cam 108 locks into position as lobe 116 forces clip member 102 downwardly through point of maximum compression followed by continued movement of eccentric cam 108 until following flat 118 is in substantial contact with clip member 114, allowing for a limited degree of relaxation of clip member 102 in the locked position. Probe 90 is unlocked from attachment to the animal by reversing the rotation of lever 110 thereby moving lobe 116 upwardly and out of contact with clip member 102. Clip member 102 is then allowed to relax and move upwardly under its own resilient restorative force as well as any applied forces from the animal's tissue.

Either the improved probes of FIGS. 1-5 or other probes well known to the art can be used to advantage in combination with the circuitry illustrated in the block diagrammatic view in FIG. 6. Turn now to FIG. 6 wherein an electronarcotic current is applied to a subject animal, diagrammatically denoted by reference numeral 120 to which electrical contact is made via probes 122 and 124. The details of the probe and of the manner in which electrical contact or current is arranged through animal 120 is devised according to means well known to the art, preferably using probes as discussed in connection with FIGS. 1-5. Current is supplied at a selected voltage in the range of approximately 65-125 VDC to animal 120 through a switching device 126. Switching device 126 is a conventional power transistor having a limiting resistor 128 on its output and its input coupled to a constant current generator 130. Typically, current between 5 MA and 750 MA is supplied to animal 120. Constant current generator 130 is a conventional high-voltage adjustable regulator well known in the art such as type TL-783C sold by Texas Instruments of Dallas, Tex. The output voltage of constant current generator 130 is determined by the ratio of the resistance between output 132, adjust terminal 134 and ground 136. Adjust input 134 is coupled to probe 124 which is the low potential side of the animal load 120. Thus, the ratio of resistance between output 132 and probe 124 on one hand as compared to the voltage drop across diodes 138 and 140, which serve as reference diodes for producing a constant forward voltage drop, on the other hand determines the amount of voltage at output 132 and hence across animal load 120.

Therefore, it is one of the features of the present invention that the nature of the animal load itself will provide a means for determining the current applied to the animal. Therefore, the probe-to-probe resistance through the animal serves as part of the feedback loop for determining the strength of the electronarcotic current whereby individual differences among animals and between species can be automatically compensated.

Input 142 of constant current generator 130 is coupled to the output of a conventional voltage regulator 144. In the preferred embodiment, the output of voltage regulator 144 can be manually adjusted from 65 volts DC to 125 volts DC. A conventional DC-to-DC power convertor 146 converts the 12 VDC battery supply included as a part of the unit to 125 VDC necessary for the input 148 of voltage regulator 144. In the preferred embodiment of the circuitry of FIG. 6, the unit is battery powered and portable to enhance its utility as a field unit. However, it is entirely within the scope of the invention that a conventional AC-to-DC convertor could be substituted as well as other means well known in the art to provide a regulated, adjustable voltage as the input to constant current generator 130.

What has been described thus far in connection with FIG. 6 is a circuit capable of applying a manually adjusted voltage in order to provide a current to a subject animal at a level determined by the selected voltage and the intrinsic resistance path through the animal. The additional circuitry diagrammatically depicted in FIG. 6 provides a means for automatically providing a multiplicity of pulsed energy levels to the subject animal according to the invention.

Switching transistor 126 is driven in turn by a driving device 150. Device 150 in turn is coupled and controlled by a pulse mixer and modulating module 152. In the preferred embodiment, module 152 is a general purpose CMOS RC Timer of the type manufactured by Intersil of Sunnyvale, Calif., as model ICM 7555/6 or NE 556N or its equivalent. Pulse mixer and modulating module 152 mixes pulses from three frequency generators. A first frequency generator 154 selectively generates an approximately 60 to 180 Hz frequency at its output 156 as manually adjusted. The signal 157 on output 156 is shown in a graphic time line (a) in FIG. 7. Master pulse generator 158 in turn generates a master pulse 159 of 1.2-2.1 milliseconds width at output 160 of FIG. 6 as referenced by the same numeral in FIG. 7. The signal output at 160 of master pulse generator 158 is synchronized to the selected signal on output 156 of frequency generator 154. Finally, a third generator, a slave modulating generator 162 in FIG. 6 is similarly synchronized to master pulse generator 158 and generates a 300 microsecond width modulating pulse shown in FIG. 7 as line (b).

Turn now to FIG. 7 wherein the modulation of these frequencies from generators 154, 158 and 162 and their output from pulse mixer and modulating module 152 can now be understood. A selected frequency at output 156 generates a train of pulses shown in line (a) which are approximately 16.7 to 5.5 millisecond apart. Output 156 is coupled to master pulse generator 158 and serves as a trigger for the generation of a master pulse which has an adjustable pulse width from 1.2-2.1 milliseconds. Again, manual adjustment of the master pulse width (signal 159 line (a)) is provided by conventional means in master pulse generator 158. Similarly, slave modulating generator 162 is synchronized to master pulse generator 158 and is characterized by frequency of the order of 3.333 Khz with an adjustable duty cycle of approximately 10 to 90 percent. Again, the duty cycle of output 164 of slave generator 162 is manually adjustable according to conventional means.

Therefore, returning to FIG. 6, master pulses 159 are then coupled to module 152 at a rate determined by selected frequency generator 154. Simultaneously, a synchronized slave frequency signal 165 shown in line (b) FIG. 7 on output 164 with a selected duty cycle is also provided to module 152. These signals are mixed within module 152 to produce an output signal 166, depicted in the time graph of FIG. 7 on line (3) as 3.333 Khz signals of selected duty cycle in groups of duration equal to the width of master pulse 159 and repeated with a group reptition rate of the selected frequency 157. Output signal 166 is coupled from output 167 to the base of transistor device 150, which in turn controls switching transistor 126, to similarly modulate the output 132 of constant current generator 130 through animal load 120.

In most animals, the neural muscular frequency is on the order of 20 to 30 Hz, therefore according to the invention, changes in the electroanalgesic energy level faster than 50 to 33 milliseconds are likely to have minimal effect. Once neuromuscular blocking has been established, it will likely be maintained as long as an electronarcotic current is present in the animal tissue every 30 to 50 milliseconds according to the invention. Therefore, according to the present invention, the total energy transferred to the animal is reduced by a duty cycle modulation through the slave modulating generator 162 which nevertheless continues to have a group repetition rate which continues to interfer or block the neuromuscular activity. By this means, immobilization is maintained while avoiding disabling or destructive interference with respiratory and cardiac functions.

FIG. 6 includes an additional feature of the invention wherein an open alarm circuit 168 provides an audible and visual means for indicating an open circuit between probes 122 and 124. If, for example, good electrical contact is lost with animal load 120, the entire voltage drop then essentially appears across limiting resistor 128 so that a low potential is then fed back to input 134 of constant current generator 130 to thereby reduce the current output. When animal load 120 becomes substantially open circuited, the voltage on sensing line 180 will no longer be defined by the potential drop across diodes 138 and 140 but will be allowed to float which will be interpreted by module 152 to generate an alarm pulse on input 182 of open alarm and lamp circuit 168. Alarm circuit 168 will then latch-on a flashing light and/or audible alarm. This will alert the practitioner so that injury and pain can be prevented either to the animal or the practitioner by the open circuit across probes 124 and 122.

In the preferred embodiment, module 152 and generators 154, 158 and 162 are configured from a dual CMOS timer sold as Model NE 556 by Intersil of Santa Clara, Calif. The dual timer can be configured as an astable multivibrator with a variable duty cycle which is manually adjusted by a potentiometer. Thus, in the dual package NE 556, one CMOS timer is configured as an astable multivibrator with a frequency of 3.333 Khz and variable duty cycle, while the other timer is configured as the master generator with a selected frequency between 60 and 180 Hz and a similarly varied duty cycle so that the pulse widths are between 2.1 and 1.2 milliseconds. The master pulse generator and slave modulating generator are synchronized and combine in a NAND logic gate to generate the timing curve (line c) 166 of FIG. 7. Switch 184 is used as an input to one NAND gate to enable or disable the master frequency from being mixed in a second NAND gate with the slave frequency. Thus, when switch 184 is closed, the slave frequency as shown on line (b) will be provided as output 166 without modulation by the master frequency shown on the timing diagram line 156. Similarly, the mixing NAND gate in module 152 will be disabled by an open alarm and lamp circuit 168 when an open circuit across animal load 120 is sensed, thereby causing output 167 to go below and remain low thereby shutting off device 150. In turn switching device 126 prevents the flow of additional electronarcotic current through probes 122 and 124 until electrical continuity between the probes is again established.

Figure 8:
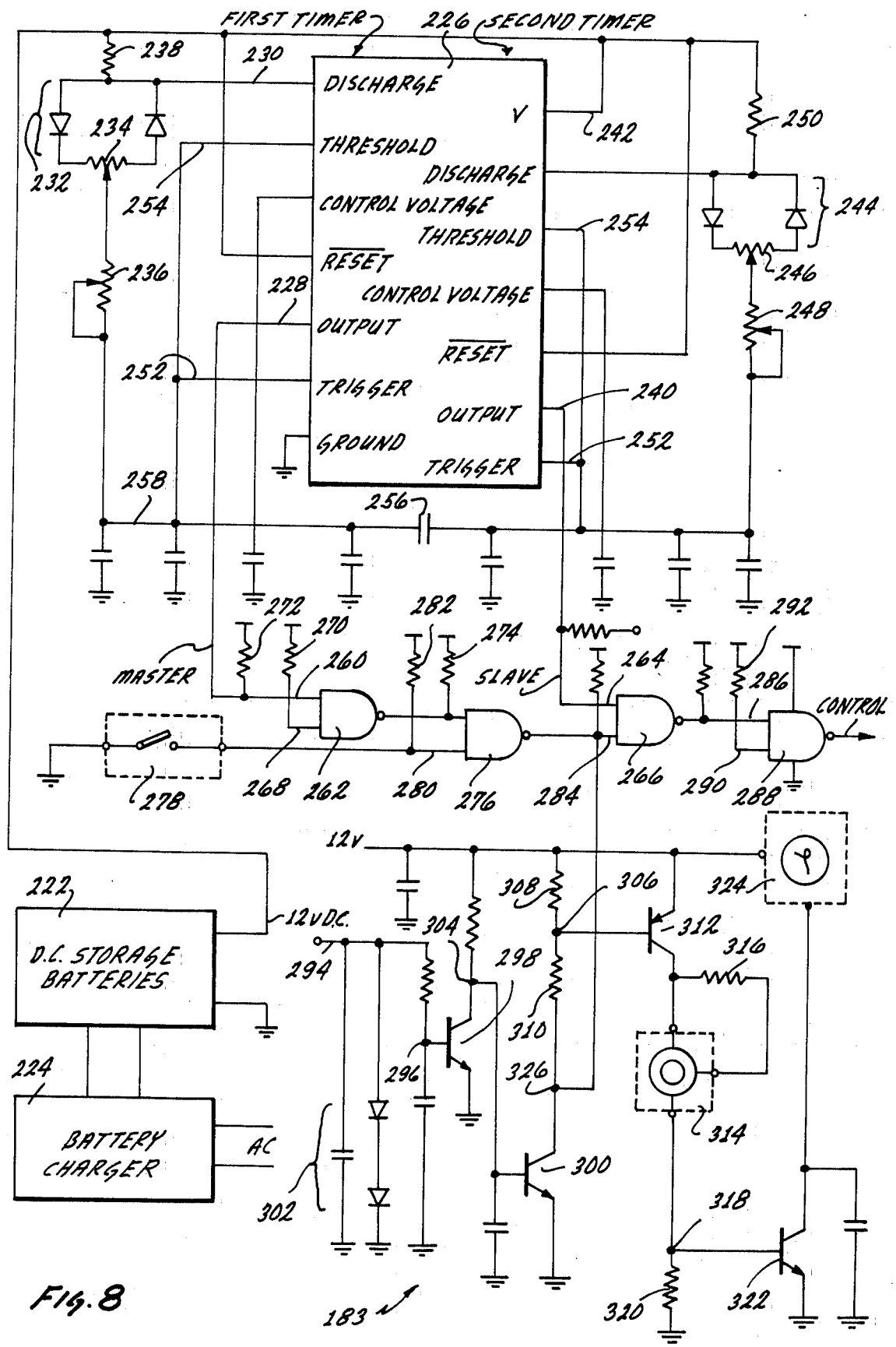
FIG. 8 is a detailed schematic of one embodiment of a portion of the circuitry shown in diagrammatic view in FIG. 7.
Figure 9:
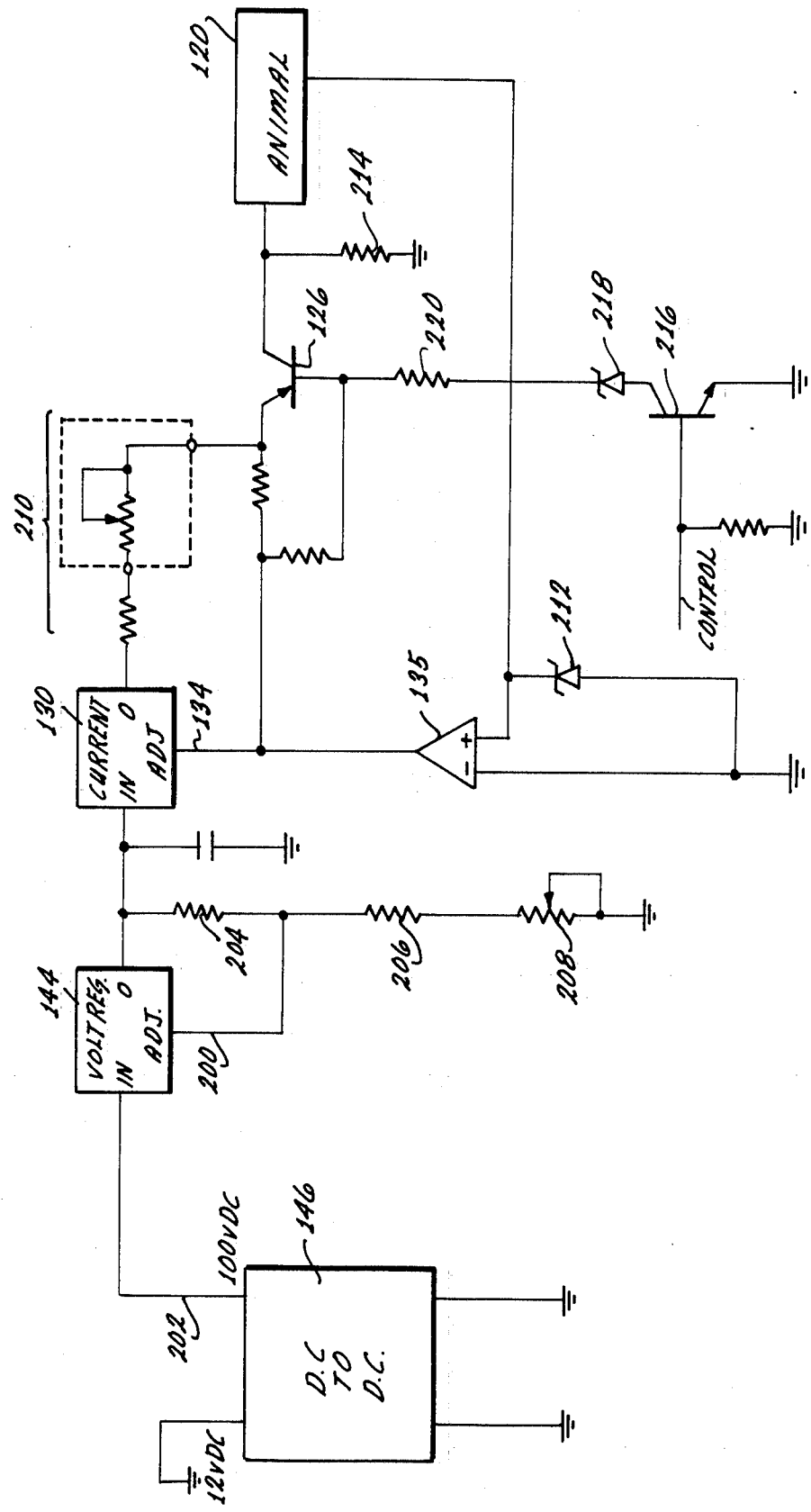
FIG. 9 is a detailed schematic of one embodiment of the remaining portion of the circuitry shown in diagrammatic view in FIG. 7.

The circuitry which has been described above is illustrated in one embodiment in greater detail in connection with FIGS. 8 and 9. Turn first to FIG. 9, wherein schematic of one embodiment of the upper portion of the circuitry of FIG. 6 is described. A conventional DC-to-DC convertor 200 is coupled to a 12 VDC source, such as a wet storage cell. Means may be included (shown in FIG. 8) for providing an AC-to-DC charge of the wet storage cell. In any case, the illustrated embodiment is a portable unit well adapted for field use. DC-to-DC convertor 200 is conventional in design and converts the 12 VDC to an alternating current which is stepped up across the transformer. The output of the transformer is then fully rectified at the higher output voltage. In the illustrated embodiment 100 VDC is provided at output 202.

The output of DC-to-DC convertor 200 is coupled to the input of voltage regulator 144. As previously described, the output of voltage regulator 144 is fixed according to a feedback current provided to an adjust input 200. The signal to adjust input 200 is provided by a resistance ladder comprised of resistors 204, 206 and variable resistor 208. Thus, variable resistor 208 provides a means for manual adjustment for the operating base point of the system.

The output of voltage regulator 144, again as previously described in connection with FIG. 6, is provided to the input of a constant current generator 130. As described, constant current generator 130 is a unit identical to voltage regulator 144. The output of current generator 130 is coupled through an adjustable current limiting resistive network 210 to the input of switching transistor 126, again described in connection with FIG. 6. The output of switching transistor 126 is coupled to animal load 120 which in turn is coupled to ground through Zener diode 212 which defines a reference voltage. Resistor 212 on the output of switcher resistor 126 provides a high resistive load to prevent inadvertent shock to the user in the case when no animal load 120 is coupled to the circuit.

Assume for the moment that switching transistor 126 is conductive. The resistive of animal load 120 functions in much the same manner as variable resistance 208 does with respect to voltage regulator 144. The variable resistance of animal load 120 is sensed through a differential amplifier 135 whose other input is coupled to ground. The output of differential amplifier 135 is coupled to adjust terminal 134 of constant current generator 130. Thus, the output and adjust circuitry of constant current generator 130 is functionally analogous to the same feedback circuitry illustrated in connection with voltage regulator 144. However, the difference is that the variable resistive element in the output circuitry of constant current generator 130 is the animal load 120. Furthermore, current delivered to the animal load 120 is controlled by switching transistor 126. The base of switching transistor 126 is coupled in turn to a driving transistor 216 through a Zener diode 218 and biasing transistor 220. Driving transistor 216 in turn is controlled by a control signal coupled through its base. The control signal is generated by the circuitry illustrated in FIG. 8 and shown in one case as line 166 in FIG. 7.

Turn now to FIG. 8 wherein alarm and timing circuitry as generally described in connection with the lower portion of FIG. 6 is described in greater detail. Again, the circuitry is powered by DC storage batteries 222, which may be charged as desired by conventional AC battery charger 224. The timing signals of FIG. 7 are generated by the dual timer 226, which as previously stated, is a CMOS timer sold as model NE 556 by Intersil of Santa Clara, Calif. Consider first the signals shown for a first timer on the left side of dual timer 226. Output 228 is the signal MASTER depicted by pulse train 156 of FIG. 7. Discharge terminal 230 is coupled capacitively to ground through a diode bridge 232 and a resistive network comprised of a variable resistors 234 and 236. By adjustment of resistors 234 and 236 together with fixed resistor 238, the discharge rate and charge rate of the signal at output 228 of the first timer can be adjusted. For example, in the illustrated embodiment wherein NE 566 is used, fixed resistor 238 is a 1K ohm resistor while variable resistor 234 is a 10K ohm potentiometer and variable resistor 236 a 20K ohm potentiometer. These resistances can be varied to produce a MASTER pulse of 1.2 to 1.1 milliseconds in width with a cycle period of 5.5 to 16.7 milliseconds as shown in line 156 of FIG. 7. It is, of course, entirely within the scope of the invention that other values and timing could be chosen according to well-understood design principles by using different numeric values.

Turn now to the second timer within the dual timer 226 as shown by the signals on the right hand side of the block diagram in FIG. 8 denoted by reference numeral 226. As before, ouput 240 of the second timer is a SLAVE signal as represented by line 164 of FIG. 7. The SLAVE signal in essence represents the duty cycle of the MASTER pulse as will be described below. Discharge terminal 242 of the second timer is similarly coupled capacitively to ground through a diode bridge 244, a variable resistor 246 and a second variable resistor 248. Again, variable resistors 246, 248 and fixed resistor 250 can be chosen to produce a pulse width and frequency as desired. Again, in the illustrated embodiment, SLAVE signal is chosen to have a frequency of approximately 3.333 kilohertz with an adjustable duty cycle of 10–90%. The duty cycle of the SLAVE signal is determined by adjustment of the variable resistor 246 while its frequency is determined by the adjustment of variable resistor 248. Again in the illustrated embodiment, fixed resistor 250 is a 1K ohm resistor, variable resistor 246 a 250K ohm resistor, and variable resistor 248 a 100K ohm resistor. Again, many other numerical values could be chosen according to well understood design principles in order to derive a SLAVE signal with different frequencies or duty cycle ranges.

The TRIGGER and THRESHOLD terminals 252 and 254, respectively, of both the first and second timer are similarly capacitatively coupled to ground and through each other by means of capacitor 256 so that the trigger signal of both the first and second timers are synchronized as indicated by the leading edge synchronization of waveforms 156 and 164 in FIG. 7. The remaining inputs to the first and second timer such as CONTROL VOLTAGE and RESET are inactivated by holding RESET logically high by direct connection to the power supply and control voltage capacitively grounded through an independent circuit whereas THRESHOLD and TRIGGER terminals 252 and 254 for the first and second timer are each capacitatively ground through a common connection to line 258. The same line 258 also provides the capacitively coupled ground for the discharge networks of the first and second timer as described above.

The result is that a MASTER signal of the form of line 156 in FIG. 7 is provided at input 260 of NAND gate 62 and a SLAVE signal of the form of line 164 of FIG. 7 is provided at input 264 of NAND gate 166. Consider first the MASTER signal. The other input 268 of NAND gate 262 is coupled through a pull-up resistor 272, the 12 VDC supply. Similarly, a pull-up resistor 272 is coupled to input 260 to precharge the line. Thus, NAND gate 262 acts as an invertor and supplies MASTER to input 274 of NAND 276. The other input of NAND gate 276 is coupled to a switch 278 which, as will be described in a moment, is used to disable the pulsed charge and to provide an unpulsed modulated voltage to animal load 120. Thus, switch 278 provides a manual means of coupling input 280 to ground, otherwise input 280 will be pulled high through a pull-up resistor 282.

Assume for the moment that switch 278 is open so that input 280 is pulled high. NAND gate 276 will once again act as an invertor to deliver the signal, MASTER, to input 284 of NAND gate 266. However, the other input 264 of NAND gate 266 as stated above is the signal, SLAVE. The output of NAND gate 266 is thus always high unless both SLAVE and MASTER signals are simultaneously high, in which case the output of NAND gate 266 is a logical low. The output of NAND gate 266 is provided as an input 286 to NAND gate 288. The other input 290 of NAND gate 288 is pulled high through a pull-up resistor 292. Thus, NAND gate 288 acts as an invertor of the NAND function of the signals, SLAVE and MASTER. Therefore, the output of NAND gate 288, signal control, will always be logically low unless both the signals MASTER and SLAVE are logically high, in which case the signal control will be logically high as well. The signal, CONTROL, is thus shown as waveform 166 in FIG. 7. As described in connection with FIG. 9, the signal, CONTROL, is thus applied to the base of transistor 216 which in turn drives switching transistor 126 to thereby deliver to the probes of the invention a pulsed DC current to animal load 120.

In the case where switch 278 is activated thereby coupling input 280 to ground, the output of NAND gate 276 will thus be held high regardless of the value of the signal, MASTER. In turn, the input 284 of NAND gate 266 thus being constantly held high, NAND gate 266 will simply invert the signal, SLAVE, which again will be inverted by NAND gate 288. In this instance, the control signal will appear as identical to the SLAVE signal and will be represented by the line 164 of FIG. 7. Therefore, the current delivered to animal load 120, instead of being pulsed at the MASTER frequency rate, will be continuously delivered by a pulse train with a duty cycle defined by the manual setting of variable resistor 246.

The timing circuit having now been described in detail, turn to the lower right portion of FIG. 8 wherein one embodiment of open alarm and lamp circuit 183 (FIG. 6) is illustrated. Input 294 is coupled to the lower voltage side of the probe coupled to animal load 120. Input 294 is coupled through a biasing network to base 296 of drive transistor 298. Normally, drive transistor 298 is conductive so that its collector, which is coupled to the base of trigger transistor 300 is held close to ground thereby biasing trigger transistor 300 off. However, when contact is lost with the animal, the voltage at probe V2, the low voltage probe, will float and the diode and capacitative network 302 will remove any residual bias from base 296 of drive transistor 298, thereby causing transistor 298 to turn off.

When drive transistor 298 turns off, the voltage at node 304 coupled to the collector of transistor 298 and the base of trigger transistor 300 begins to rise toward the voltage supply. Trigger transistor 300 then begins to conduct dropping the biased voltage at node 306 between two fixed serially connected resistors 308 and 310. As the voltage at node 306 then begins to fall to a biased point, transistor 312, whose base is coupled to node 306, will begin to conduct. When transistor 312 conducts, a self contained alarm unit 314 diagrammatically depicted in FIG. 8 will sound an alarm determined in part by the value of a feedback resistance 316. When alarm 314 is turned on, a voltage is impressed upon node 318 as determined in part by biasing resistor 320 coupled between node 318 and ground. As a result transistor 322 whose base is coupled to node 318 begins to conduct and provide a conductive path for a lamp 324 diagrammatically depicted in FIG. 8. Thus, alarm 314 will sound and alarm lamp 324 will be lit. Alarm lamp 324 may contain a flashing unit or, as in the illustrated embodiment, intermittant alarm unit 314 delivers an intermittent voltage to node 318 thereby flashing lamp 324 in synchronism with the audio pulses of the alarm circuit. Therefore, whenever contact is lost or the resistance of animal load 122 increases dramatically, the voltage at input 294 will either float or drop to a very low level thereby allowing the capacitive-diode network 302 to bias the base of driver transistor 298 off and ultimately sound the alarm.

Note, however, that input 284 of NAND gate 266 is also coupled to node 326 or the collector of trigger transistor 300 of the alarm circuit. When an alarm is sounded, node 326 will be pulled close to ground. A logical 0 will thus be fixed at input 284 of NAND gate 266. The output of NAND gate 266 will thus be held at a logical high no matter what the value of the signal, SLAVE, may be. NAND gate 288 as described above will invert the output of NAND gate 266 and keep the signal, CONTROL, a logical low. As long as CONTROL is a logical low, switching transistor 126 of FIG. 9 will be biased off, thereby preventing sudden inadvertent shorts or other large current drains through animal load 120 or inadvertently through the user during any open circuit configuration indicated by a loss of either one of the probe contacts.

Many modifications and alterations may be made by those having ordinary skill in the art without departing from the spirit and scope of the invention. For example, the circuitry of FIG. 6 can be altered in a number of well known ways to provide the same modulation of the electronarcotic circuit as described. For example, instead of using astable multivibrators as the frequency generators, it would be possible to provide digital control through a central processing unit subject to suitable software control, wherein the duty cycles would be keyed into the central processor memory. Therefore, it must be understood that the illustrated embodiment has been set forth only for the purposes of clarity and example, and should not be taken as limiting the invention as defined in the following claims:

I claim:

1. An apparatus for applying an electronarcotic signal to an animal comprising:
   electrode means for making and maintaining electrical contact with said animal; and
   a source for generating said electronarcotic signal, said source coupled to said electrode means, said source comprising a feedback loop coupled to said electrode means for adjusting said electronarcotic signal in accordance with the intrinsic electrical resistance path through said animal is included as a part of said feedback loop of said source, whereby individual variations among animals is automatically compensated by adjustment of said source for generating said electronarcotic signal by inclusion of the intrinsic resistance through said animal within said feedback loop of said source.

2. The apparatus of claim 1 wherein said electronarcotic signal generated by said source is modulated to have a master pulse rate in the range of 60 to 180 Hz; and
   wherein said source further comprises means for modulating said electronarcotic master pulse signal at a higher slave pulse frequency rate and with a selected duty cycle.

3. The apparatus of claim 2 wherein said master pulse rate is in the range of 2.1 to 1.2 milliseconds.

4. The apparatus of claim 1 wherein said source generates said electronarcotic signal with a modulation having pulses reproduced at a group rate at the same order of magnitude as neuromuscular signals within said animal, said pulses having a selected duty cycle in order to selectively reduce energy imparted by said source through said electrode means to said animal.

5. A method for immobilizing an animal by passing an electronarcotic current through said animal comprising the steps of:
   generating a direct current at a preselected voltage for an application to said animal;
   applying said direct current to said animal;
   feeding back a portion of said current applied to said animal to said source generating said direct current in accordance with the intrinsic resistance of said animal; and
   adjusting said direct current generated by said source and applied to said animal in response to said current fed back from said animal to said source,
   whereby the intrinsic resistance of said animal is included within a feedback path for said source for generating said direct current so that the amplitude of said direct current is adjusted to accommodate individual electrical characteristics of said animal.

6. A method of claim 5 where in said step of generating said direct current, said direct current is pulsed at a first frequency at approximately the same frequency as neuromuscular signals within said animal.

7. The method of claim 6 where in said step of generating said pulsed direct current, said pulsed direct current is further modulated to form groups of pulses, said groups having said first frequency and said pulses having a higher second frequency in order to reduce the amount of energy transferred to said animal by said electronarcotic signal.

8. The method of claim 7 further comprising the step of modulating said pulsed electronarcotic signal at said second frequency with a selected duty cycle chosen to maintain a holding energy level for immobilization at a minimal energy.

9. A method for immobilizing an animal by producing an electronarcotic signal through said animal comprising the steps of:
   generating a pulsed DC signal characterised by a master pulse rate of a first frequency wherein each master pulse width comprises a plurality of pulses of a higher second frequency repeated at a group rate of said first frequency;
   selectively applying said signal to said animal in order to initially provide a blocking energy level for causing initial immobolization by a nonmodulated pulsed direct current, and secondly to maintain a holding energy level by selectively modulating said pulses of said first frequency with said pulses of said second higher frequency.

10. The method of claim 9 where the step of generating said pulsed direct current signal includes selectively modulating said pulsed direct current signal with said pulses of said second frequency at a selected duty cycle to thereby vary the energy transferred into said animal.

* * * * *